United States Patent
Bodmann et al.

(10) Patent No.: US 7,038,072 B2
(45) Date of Patent: May 2, 2006

(54) PROCESS FOR MONOALKYLATION OF C-H ACIDIC METHYLENE GROUPS

(75) Inventors: Kerstin Bodmann, Marl (DE); Oliver Meyer, Münster (DE); Manfred Kaufhold, Marl (DE); Jürgen Fieker, Herten (DE); Renate Paulczynski, Herne (DE)

(73) Assignee: Degussa AG, Düsseldorf (DE)

( * ) Notice: Subject to any disclaimer, the term of this patent is extended or adjusted under 35 U.S.C. 154(b) by 352 days.

(21) Appl. No.: 10/622,779

(22) Filed: Jul. 21, 2003

(65) Prior Publication Data

US 2004/0054226 A1 Mar. 18, 2004

(30) Foreign Application Priority Data

Jul. 24, 2002 (DE) ................ 102 33 507

(51) Int. Cl.
*C07C 255/01* (2006.01)
*C07C 67/30* (2006.01)

(52) U.S. Cl. ...................... 558/357; 560/203
(58) Field of Classification Search ........... 558/357; 560/203
See application file for complete search history.

(56) References Cited

U.S. PATENT DOCUMENTS

| 4,476,106 A | 10/1984 | Bardy et al. ............ 424/1.1 |
| 5,510,509 A | 4/1996 | Steffen ................. 560/124 |
| 6,262,298 B1 | 7/2001 | Metz et al. ............. 560/203 |
| 6,462,224 B1 | 10/2002 | Harthun et al. .......... 560/124 |
| 2001/0007040 A1 | 7/2001 | Harthun et al. .......... 560/124 |

FOREIGN PATENT DOCUMENTS

| DE | 3401913 A1 | 8/1985 |
| DE | 43 26 917 C1 | 8/1993 |
| DE | 197 52 041 A1 | 5/1999 |
| DE | 199 63 115 A1 | 7/2001 |
| EP | 0 069 648 A1 | 1/1983 |

OTHER PUBLICATIONS

English language abstract for EP 0 069 648, Reference AG1 above.
English language abstract for DE 197 52 041, Reference AH1 above.
English language abstract for DE 199 63 115, Reference AI1 above.
English language abstract for DE 3401913, Reference AJ1 above.
English language abstract for DE 43 26 917, Reference AK1 above.
White, "Alkylations with Potassium Carbonate in Dimethlyformamide," *Synthetic Communications* 7(8):559-568 (1977).

*Primary Examiner*—Kamal A. Saeed
(74) *Attorney, Agent, or Firm*—Michael A. Sanzo; Fitch, Even, Tabin & Flannery

(57) ABSTRACT

The present invention is directed to a process for the synthesis of monoalkylated C—H acidic methylene group-containing compounds, such as malonic esters, and malonic ester nitriles.

7 Claims, No Drawings

PROCESS FOR MONOALKYLATION OF C-H ACIDIC METHYLENE GROUPS

CROSS REFERENCE TO RELATED APPLICATIONS

The present application claims priority to German Application No. 102 33 507.9, filed Jul. 24, 2002, which is incorporated in its entirety herein by reference.

FIELD OF THE INVENTION

The present invention relates to a process for alkylating C—H acidic compounds. In particular, the invention is directed to the selective production of monoalkylation products, starting from C—H acidic methylene group-bearing substrates and dihalogen alkanes in a non-aqueous system.

BACKGROUND OF THE INVENTION

The alkylation of C—H acidic compounds is a standard reaction of organic chemistry. One problem encountered in carrying out this reaction is that it is difficult to suppress dialkylation reactions. This is because, especially with strongly C—H acidic compounds, the acidity of the monoalkyl derivative is usually sufficient to promote further reaction with an electrophile. Since the singly and doubly alkylated derivatives are often difficult to separate, this can be a problem in situations where a high degree of selectivity is required (Organikum, VEB Deutscher Verlag der Wissenschaften, Berlin, p. 517, 1986).

Previously described methods for the alkylation of strongly C—H acidic compounds, such as malonic esters or nitriles of malonic esters, have used sodium ethanolate or sodium hydride to produce deprotonated derivatives. These are subsequently trapped with an electrophile, for example an alkyl halide, in a substitution reaction (DE 3401913; EP 69648). There have also been attempts to use potassium carbonate as the base for alkylating malonic esters (*Synth. Commun.* 7:559–568 (1977); *Zh Org. Khim.* 19:474–480 (1983); DE 4326917). Although the references disclosing these procedures were primarily concerned with dialkylating malonic ester derivatives with 1,2-dihalogen alkanes to form cyclopropyl derivatives, the monoalkylation of malonic esters has also been disclosed. DE 19752041 describes a monoalkylation reaction which utilizes a molar ratio of malonic acidic derivative to alkylating agent to potassium carbonate of 1:1.5–3.0:0.4–0.6. The reference proposes that dialkylation may be accomplished by using quantity of base greater than or equal to 1 in relation to the C—H acidic compound.

OBJECT OF THE INVENTION

The object of the present invention was to provide a new process for producing monoalkylation products from C—H acidic compounds, especially from malonic ester derivatives. This process should be useable on an industrial scale, economical and ecologically acceptable. The process developed was found to yield a higher percentage of monoalkylation products than previously described processes.

A second object of the invention was to provide a production process that allows one to produce ω-halogen carboxylic acids or ω-halonitriles from the corresponding malonic ester derivatives under conditions that can be carried out on an industrial scale.

SUMMARY OF THE INVENTION

The present invention is directed to a process for monoalkylating C—H acidic methylene groups by reacting a methylene group-bearing substrate with dihalogen alkanes in which the two halogen atoms are separated by a chain of at least 3 carbon atoms. The reaction is preferably carried out in a polar aprotic solvent and water formed during the reaction is continuously removed, e.g., using a cyclic hydrocarbon or an aromatic hydrocarbon as an entrainer. Also included in the reaction is a phase transfer catalyst and alkali carbonates or alkaline earth carbonates which, in their aggregate, are present in a molar ratio relative to the methylene group-bearing substrate of greater than 0.6:1, and preferably in a ratio of greater than 1:1. In preferred embodiments, the phase transfer catalyst is continuously metered, i.e. slowly and steadily added, into the reaction mixture from the start of the reaction. The preferred methylene group-bearing substrate is a 1,3-dicarbonyl compound, the preferred carbonate is potassium carbonate and the preferred phase transfer catalyst is a quaternary ammonium salt. The solvent is preferably DMF (dimethylfluoride), DMSO (dimethylsulfoxide), dimethylacetamide or N-methylpyrrolidone.

In one particularly preferred embodiment the process described above is performed such that the methylene group-bearing substrate, the dihalogen alkane and the aggregate of alkali carbonates and alkaline earth carbonates are present in a ratio of 1:2.0–5.0:1.0–2.0. The same preferences described above with respect to reaction conditions and compounds used apply to reactions carried out with this range of ratios.

The present invention also includes a process for producing a ω-alkyl halide nitrile or ω-halogen carboxylic acid by reacting a malonic acid diester or cyanoacetic acid ester with a α,ω-dihalogen alkane in which the two halogen atoms in the α,ω-dihalogen alkane are separated by a chain of at least 3 carbons. The preferred conditions of the reaction and the preferred compounds are as described above. The product produced then undergoes a saponification and decarboxylation reaction, preferably performed by adding a catalyst acid without the addition of a solvent, in order to make the desired ω-alkyl halide nitrile or ω-halogen carboxylic acid.

DETAILED DESCRIPTION OF THE INVENTION

Using the process described herein, it is possible to monoalkylate C—H acidic compounds with specific dihalogen alkanes in very good yields with respect to time and space. Reactions may be performed on an industrial scale while avoiding intermolecular or intramolecular dialkylation reactions. Thus, under the conditions of the invention, 1,6-dichlorohexane reacts with diesters of malonic acid within 3 hours in approximately 80% yield to form the desired monoalkylation products. This occurs without the problem of a chain forming through polyalkylation with excess base. Any bishalogenated alkane that may be selected by one of skill in the art can be used in the reaction provided that the halogen atoms are separated by a chain of at least 3 carbon atoms. Especially preferred are the use of primary or secondary dihalogen alkanes, especially α,ω-dihalogen alkanes of the formula X—$(CH_2)_n$—Y, where n=4–14; and X and Y are independently selected from fluorine, chlorine, bromine and iodine. Examples include 1,4-dichlorobutane, 1,6-dichlorohexane, 1,8-dichlorooctane, 1,10-dichlorodecane, 1,6-dibromohexane, and 1,8-dibromooctane. For environmental and cost reasons, chlorides will generally be the most preferred halides.

The ratio of alkali carbonates or alkaline earth carbonates to methylene group-bearing substrates is preferably greater than 1:1, more preferably greater than 1.1:1, still more preferably greater than 1.3:1, and still more preferably greater than 1.4:1. An upper limit for the quantity of base may be determined by one of skill in the art based upon accepted industrial and commercial criteria. For example, the amount added may be limited by the stirability of the suspension or by cost constraints. Although one of skill in the art is free to choose the quantity of base for optimal reaction conditions, as a general guide, a ratio of approximately 1.5:1 (base:C—H acidic compound) has proven to give good results.

In a preferred embodiment, the phase transfer catalyst is added continuously to the reaction mixture, starting from the beginning of the alkylation reaction. This permits one to carefully control the exothermal and gas-forming reaction and may further increase the rate of reaction. This may be contrasted with procedures in which monoalkylation is obtained by adding phase transfer catalysts after approximately 50%–80% the malonic ester has reacted (see e.g., DE 19752041). Optionally, a second reaction lasting ¼–⅔ of the total reaction time can follow after the end of the addition of the catalyst. The end of the reaction can be ascertained by the abating gas and the development of water.

C—H acidic methylene group-bearing molecules are well known in the art and those that are strongly acidic are preferred for use in the present method. Compounds with strongly acidic C—H methylene groups are, in particular, those that, in the vicinal position, bear special groups that exert an electron-attracting I effect on the methylene group. This effect can be intensified by mesomeric effects acting in the same direction. In this regard, 1,3-dicarbonyl compounds deserve special consideration. They have carbonyl or carboxyl groups in the immediate vicinity of the methylene group providing an I and M effect, and creating an extreme C—H acidity for this class of compound. These compounds are especially preferred for the present process and are exemplified by diesters of malonic acid—with the same or different ester groups, cyanoacetic acid esters, acetoacetone, β-oxocarboxylic acid ester. Especially preferred are diesters of malonic acid, malonic acid dinitriles or cyanoacetic acid esters, preferably with primary, secondary or tertiary ($C_1$–$C_8$) alkyl groups serving as the esters.

Any alkali carbonate or alkaline earth carbonate may be used in the present invention. Sodium or potassium carbonate will generally be preferred for economic reasons with potassium carbonate being the most preferred. However, lithium carbonate and/or magnesium carbonate should also be effective. The added carbonate should preferably have a fine grain content of 85%<0.1 nm.

An essential feature of the present invention is that water that forms during the reaction must be removed from the reaction mixture. Any of the substrates known in the art to be effective for this purpose can be used, including molecular sieves, ortho esters or azeotropic entrainers. If necessary, even the added dihalogen alkanes themselves can be used. Entrainers are especially important when higher boiling alkyl halides are used. The most preferred are cyclic hydrocarbons or aromatic hydrocarbons. Especially preferred are cyclohexane, methylcyclohexane or toluene.

Suitable phase transfer catalysts for use in the invention are disclosed in DE 19752041. Especially preferred are quaternary ammonium salts, such as tetrabutylammonium bromide or tetrabutylammonium chloride. Typically, 0.1 to 5 mol % catalyst, based on the added C—H acidic compounds, should be used. Preferably, the catalyst is added in a range of 0.25 to 1 mol %, and most preferably at about 0.5 mol %. The addition can be conducted in portions as a solid or the catalyst can be dissolved in a solvent or the dihalogen alkane prior to addition.

It has proven to be advantageous to use the methylene group-bearing substrate, the dihalogen alkane and a carbonate in a molar ratio of 1:2.0–5.0:1.0–2.0. However, the preferred molar ratio is 1:2.5–3.5:1.2–1.8. The excess alkyl halide can be recovered after the reaction and recycled. Surprisingly, despite the presence of excess dihalogen alkane and carbonate, the bisalkylated products are produced in only a very small amount using the present method.

The reaction should be conducted in a polar aprotic solvent, preferably DMF, DMSO, dimethylacetamide or N-methylpyrrolidone. However, as an alternative, a singly or doubly end group terminated polyether, like polyethylene glycol, can also be used (DE 19963115). Mixtures of both solvent groups can also serve as the reaction medium. If the polyether is mixed with the polar aprotic solvent, it suffices to add at 1–20% by wt., and preferably at 5–15% by wt., based on the polar aprotic solvent. As an alternative to the polyethers, crown ethers can also be used. The addition of these reagents can lead to a better solubility of the base in the organic solvent.

The present process can carried out by adding the solvent, dihalogen alkane, carbonate base and entrainer to a receiver, and then heating the mixture to boiling. Subsequently, the phase transfer catalyst and the C—H acidic methylene group-bearing compound are metered in (either together or separately) at such a rate that gas development and reaction peaks can be kept under control. As a rule, the reaction is finished within 3 to 4 hours.

Experiments have demonstrated that when the catalyst is completely added at the start of the reaction, an unforeseeable decrease in catalytic activity is observed after a short time that results in incomplete reactions and poor yields. Therefore, it is preferable that catalyst be added continuously to the reaction mixture after the start of the reaction. Addition can be maintained over the entire period of the reaction or only during the first third to half of the reaction time. As already stated, it has proven to be especially advantageous to also meter in the C—H acidic component because this helps in controlling gas development. Reaction progress can be followed by the quantity of gas and water formed.

The reaction mixture is worked up, usually by means of simple mechanical separation of the salt and subsequent distillation of the filtrate. Both the added entrainer and the excess dihalogen alkane can be recovered during distillation and added again to the reaction. The percentage of formed bisalkylated secondary products is usually less than 5% by weight.

The invention is also directed to a process for producing ω-alkyl halide nitriles or ω-halogencarboxylic acids. In this process, malonic acid diesters or cyanoacetic acid esters are reacted with α,ω-dihalogen alkanes using the conditions and procedures described above. The products are then saponified and decarboxylated. Preferably the saponification and decarboxylation steps are conducted by adding a catalyst acid without the addition of another solvent.

In a preferred variant of the process, the raw product, obtained after separating off the entrainer and the excess alkyl halide from the monoalkylation reaction, is added directly in a subsequent saponification/decarboxylation step to produce the corresponding monoacid/mono-nitrile. Distillation of the raw product in a short path or thin layer evaporator is possible. This procedure is particularly advantageous for long chained alkylation products (n~8) because, in these cases, distillation is difficult due to high boiling points.

The monocarboxylic acid derivatives, such as ω-halogen carboxylic acid esters and ω-halonitriles, may be made by adding a small quantity of catalyst acid to the derivatives produced using the monoalkylation reaction, without the addition of a solvent. The mixture is raised to reaction temperature and then reacted with water or a short chain carboxylic acid. In this manner, the desired aliphatic ω-halogen carboxylic acid esters or ω-alkyl halide nitriles are formed by hydrolysis or acidolysis after spontaneous decarboxylation in an almost quantitative yield. Insofar as the product is an ester of a carboxylic acid, it may undergo conversion to the corresponding carboxylic acid. In this case, alcohol can be added to induce reesterification. Both acidolysis or hydrolysis as well as the optional reesterification are conducted advantageously in a temperature range of 100–200 degrees C., and preferably in the temperature range of 120–150 degrees C.

In an especially preferred embodiment, the monoalkylation products and the catalyst acid are put into a receiver without a solvent for decarboxylation, heated to reaction temperature, and water or a short chain carboxylic acid is then fed in continuously. In this manner, the low boiling components produced during the reaction are removed by distillation from the top of the column. The reaction progress can be followed by determining the quantity of carbon dioxide that is formed.

Inorganic acids can be used as the catalyst acid for hydrolysis or acidolysis. Depending upon the boiling point of the product, preferred acids are sulphonic acids, such as methanesulfonic acid, para-toluenesulphonic acid or longer chain alkylbenzenesulfonic acids. Typically, 0.5–10% by wt. of catalyst acid are used, based on the added derivatives, such as malonic esters or cyanoacetic acid esters. In a preferred implementation, 2 to 5% by wt. of catalyst is added.

In the case of substituted alkyl esters of malonic acid, the carboxylic acid is, to a degree, reesterified with the corresponding alcohol after complete hydrolysis. In a preferred variant, the alcohol is fed directly into the bottom, raised to reaction temperature, and the liberated water is removed by distillation from the top of the column of the reaction vessel.

The carboxylic acid esters or alkyl nitriles can be purified in either a distillation column or a short path or thin layer evaporator. The remaining high boiling catalyst acid can be added back into the reaction. Using the process, desired carboxylic acid esters and alkyl nitriles are obtained in very high purity and with yields of up to 95% of the theoretical. The compounds that are to be preferably produced are: 8-chloro octanoic acid ethyl ester, 10-chlorodecanoic acid ethyl ester as well as 8-bromooctanoic acid ethyl ester.

Definitions

Alkyl/alkane is defined as a linear or branched ($C_1$–$C_{15}$) alkyl/alkane, preferably a ($C_1$–$C_8$) alkyl/alkane, such as methyl, ethyl, propyl, isopropyl, butyl, tert. butyl, sec. butyl, isobutyl, pentyl, hexyl, dodecyl—etc.

Halogen is defined within the scope of the invention as a fluorine, chlorine, bromine or iodine.

The following nonlimiting examples are provided to help in understanding the process of the invention.

EXAMPLES

Example 1

Alkylation of Diethyl Malonate with 1,6-dichlorohexane 400 g (3.0 mol) 1,6-dichlorohexane, 207 g (1.5 mol) potassium carbonate, 200 ml DMF and 300 ml cyclohexane are added to a 2 liter reaction vessel with a 50 cm column, cooler and water removal circulator, at room temperature. The water removal circulator is additionally filled with 45 ml cyclohexane. The reaction mixture is heated to the boiling point with stirring, so that the distillate, condensed at the top of the column, is passed into the water removal circulator and then directly back into the reaction bottom. At the same time 160 g diethyl malonate (1.0 mol) and a solution of 1.6 g tetrabutylammonium bromide in 65 g 1,6-dichlorohexane are metered in within 1 hour. The reaction progress can be followed by means of the quantity of gas that develops and the quantity of water that is formed. After another 2 hours, the reaction is finished (DEM conversion>99%); and the reaction mixture is cooled, filtered and washed with cyclohexane. The filtrate is then distilled in a vacuum. In so doing, 206 g (0.74 mol) 6-chlorohexyl diethyl malonate are obtained (yield: 74%, purity>99%).

Example 2

Alkylation of Diethyl Malonate with 1,6-dichlorohexane

In the apparatus described in example 1, 400 g (3.0 mol) 1,6-dichlorohexane, 207 (1.5 mol) potash, 6.3 g polyethylene glycol monomethyl ether (M500) and 345 ml cyclohexane are put into the receiver at room temperature and heated to boiling with stirring. At the same time, 160 g DEM (1.0 mol) and a solution of 1.6 g tetrabutylammonium bromide in 65 g 1,6-dichlorohexane are metered in over one hour. After another 2 hours of secondary reaction time, (DEM conversion>99%), the reaction mixture is cooled, filtered, washed with cyclohexane, and the filtrate is distilled in the vacuum. 218 g (0.78 mol) 6-chlorohexyl diethyl malonate are obtained (purity>99%, yield: 78%).

Example 3

Alkylation of Diethyl Malonate with 1,8-dichlorooctane

Analogous to the process described in example 1, 659 g (3.6 mol) 1,8-dichlorooctane and 248 g (1.75 mol) potassium carbonate are reacted with 192 g DEM in the presence of 2 g tetrabutylammonium bromide, 7.6 g polyethylene glycol monomethyl ether (M500), 400 ml cyclohexane and 50 ml DMF. Upon complete DEM conversion (>99%, approximately 3 hours), the reaction is finished and the mixture is worked up as described in example 1.283 g 8-chlorooctyl diethyl malonate are obtained (purity>99%, yield: 77%).

Example 4

Alkylation of Diethyl Malonate with 1,6-dibromohexane

Analogous to the process described in example 1, 2,045 g (8.38 mol) 1,6-dibromohexane and 579 g (4.19 mol) potassium carbonate are reacted with 448 g (2.79 mol) diethyl malonate in the presence of 17.6 g polyethylene glycol monomethyl ether (M500), 4.5 g tetrabutylammonium bromide and 950 ml cyclohexane. 701 g 6-bromohexyl diethyl malonate are obtained (purity>99%, yield: 78%).

Reference Example 1

Potash Alkylation with Catalyst in the Receiver

A mixture comprising 622 g potassium carbonate (4.5 mol), 18.9 g polyethylene glycol monomethyl ether (M 500), 1,396 g (9.0 mol), 1,6-dichlorohexane, 4.8 g tetrabutylammonium bromide and 950 ml cyclohexane is put into the receiver and heated to boiling in the water removal circulator. 481 g (3.0 mol) diethyl malonate are metered into the reaction mixture within 2 hours. After another 4 hours reaction time, the DEM conversion is only 59%. After workup of the reaction mixture and distillation, 308 g 6-chlorohexyl diethyl malonate are obtained (yield: 37%).

Reference Example 2

Alkylation of Diethyl Malonate with 1,6-dichlorohexane with Addition of Sodium Ethanolate as Base According to DE 3401913, 10 mol diethyl malonate are added drop-by-drop to a solution of 10 mol sodium ethylate in 4.5 liters of dry ethanol at 70 degrees C. In this manner the sodium salt of the diethyl malonate is formed. The solution is stirred still warm into a mixture that is boiling under reflux and comprises 5 liters of dry ethanol and 20 mol 1,6-dichlorohexane. After complete reaction, the ethanol is removed under vacuum and the residue is absorbed with chloroform. After siphoning off the resulting salt and removal of the chloroform in the vacuum, the product is fractionally distilled in vacuum (yield 65%). In this chemical reaction up to 500 g undesired bisalkylated secondary products, in particular 2,2-bis-(6-chlorohexyl)-diethyl malonate and 2,9-bis-ethoxycarbonyl diethyl decanedioate, could be isolated.

Example 7

Conversion of 2-(6-chlorohexyl)-diethyl Malonate to 8-chlorooctanoic Acid Ethyl Ester In a 500 ml reaction vessel with cooler and column, 1 mol 2-(6-chlorohexyl)-diethyl malonate and 5% by wt. Marlon® AS3 acid are put into the receiver at 150 degrees C. Over a period of 3 hours, 3 mol water are metered in and the liberated ethanol is removed by distillation from the top of the column as a mixture with water. After complete reaction of the educt, 3 mol ethanol are passed within 3 hours into the hot bottom. The resulting reaction water is separated off from the top of the column and the partially produced 8-chlorooctanoic acid is reesterified. Following distillation of the residue in vacuum, 8-chlorooctanoic acid ethyl ester with a purity of >99% and in a yield of 95% of the theoretical is obtained.

Example 8

Conversion of 2-(8-chlorooctyl)-diethyl Malonate to 10-chloro Decanoic Acid Ethyl Ester Analogous to the process described in example 7, 1 mol 2-(8-chlorooctyl)-diethyl malonate with 5% by wt. Marlon® AS3 acid at 150 degrees C. is put into the receiver. Over a period of 3 hours, 3 mol water are metered in and the liberated ethanol is removed by distillation from the top of the column as a mixture with water. After complete reaction of the educt, 3 mol ethanol are passed within 3 hours into the hot bottom. The resulting reaction water is separated off from the top of the column and the already formed 10-chlorooctanoic acid is reesterified. Following distillation of the residue in vacuum, 10-chloro decanoic acid ethyl ester with a purity of >99% and in a yield of 90% of the theoretical is obtained.

Example 9

Conversion of 2-(6-bromohexyl)-diethyl Malonate to 8-bromo Octanoic Acid Ethyl Ester Analogous to the process described in example 7, 1 mol 2-(8-bromohexyl)-diethyl malonate with 5% by wt. Marlon® AS3 acid at 150 degrees C. is put into the receiver. Over a period of 3 to 4 hours, 4 mol water are metered in and the liberated ethanol is removed by distillation from the top of the column as a mixture with water. After complete reaction of the educt, 4 mol ethanol are passed within 3 to 4 hours into the hot bottom. The reaction water is separated off from the top of the column and the partially resulting 8-bromooctanoic acid is reesterified. Following distillation of the residue in vacuum, 8-bromo octanoic acid ethyl ester with a purity of >99% and in a yield of 90% of the theoretical is obtained.

Example 10

Alkylation of Diethyl Malonate with 1,6-dichlorohexane

Analogous to the process described in example 1, a suspension comprising 622 g potassium carbonate, 1,200 g 1,6-dichlorohexane, 18.9 g polyglycol M500 and 800 ml cyclohexane was heated to boiling; and then, within one hour, 481 g diethyl malonate was added. Following completion of the DEM addition, a solution of 4.8 g TBAB in 195 g dichlorohexane was added drop-by-drop within one hour. The reaction progress could be followed by means of gas development.

| Reaction Time: | Quantity of Gas: | Conversion: |
| --- | --- | --- |
| 1 hour | 0.2 liters | 0.6% |
| 2 hours | 2.6 liters | 7% |
| 4 hours | 17.8 liters | 51% |
| 6 hours | 35.1 liters | 100% |

Workup and cleaning, analogous to example 1, yielded 625 g 6-chlorohexyl malonic acid diethyl ester (75% yield).

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A process for producing a ω-alkyl halide nitrile or ω-halogen carboxylic acid, comprising:
   a) reacting a malonic acid diester or cyanoacetic acid ester with a α,ω-dihalogen alkane, wherein:
      i) the two halogen atoms in said α,ω-dihalogen alkane are separated by a chain of at least 3 carbon atoms;
      ii) the reaction is carried out in the presence of one or more alkali carbonates or alkaline earth carbonates and a phase transfer catalyst with the constant removal of water formed during the reaction; and
      iii) said one or more alkali carbonates or alkaline earth carbonates are, when added together, present in a molar ratio to the malonic acid diesters or cyanoacetic acid esters of greater than 0.6:1; and
   b) saponifying and decarboxylating reaction products produced in step a).

2. The process of claim 1, wherein the saponification and decarboxylation are performed by adding a catalyst acid without the addition of a solvent.

3. The process of claim 1, wherein the reaction between said malonic acid diester or cyanoacetic acid ester and said α,ω-dihalogen alkane takes place in a polar aprotic solvent and wherein said one or more alkali carbonates or alkaline earth carbonates are present in a molar ratio to the malonic acid diesters or cyanoacetic acid esters of greater than 1:1.

4. The process of claim 3, wherein said polar aprotic solvent is selected from the group consisting of: DMF, DMSO, dimethylacetamide or N-methylpyrrolidone.

5. The process of any one of claims 1–4, wherein said the malonic acid diesters or cyanoacetic acid esters, said α,ω-dihalogen alkane, and said one or more alkali carbonates or alkaline earth carbonates are added in a ratio of 1:2.0–5.0:1.0–2.0.

6. The process of any one of claims 1–4, wherein a cyclic hydrocarbon or an aromatic hydrocarbon is used as an entrainer to remove reaction water.

7. The process of any one of claims 1–4, wherein a quaternary ammonium salt is used as said phase transfer catalyst.

* * * * *